United States Patent [19]

Ribolla et al.

[11] Patent Number: 4,870,727
[45] Date of Patent: Oct. 3, 1989

[54] METHOD FOR DETECTING ANOMALIES IN CORDUROY PREPARATION

[75] Inventors: G. Carlo Ribolla, Bergamo; Federico Taroni, Curno; Domenico Peiretti; Antonio Pepino, both of Turin, all of Italy

[73] Assignee: Leglertex S.r.l., Italy

[21] Appl. No.: 72,870

[22] Filed: Jul. 14, 1987

Related U.S. Application Data

[62] Division of Ser. No. 683,592, Dec. 19, 1984, Pat. No. 4,701,985.

[30] Foreign Application Priority Data

Dec. 22, 1983 [EP] European Pat. Off. ............ 83810611

[51] Int. Cl.⁴ .......................................... D06C 13/08
[52] U.S. Cl. .................................................. 26/10 C
[58] Field of Search ...................... 26/9, 10 R, 10 C; 66/157, 166

[56] References Cited

U.S. PATENT DOCUMENTS

| | | | |
|---|---|---|---|
| 555,416 | 2/1896 | Alsina | 26/10 R |
| 3,490,253 | 1/1970 | Sick et al. | |
| 3,898,469 | 8/1975 | Nichols et al. | |
| 3,977,055 | 8/1976 | Gilpatrick | 26/9 |
| 3,982,309 | 9/1976 | Gilpatrick | 26/9 |
| 4,004,239 | 1/1977 | Clarke | |
| 4,013,367 | 3/1977 | Nagao et al. | |
| 4,048,510 | 9/1977 | Clarke et al. | |
| 4,131,803 | 12/1978 | Takematsu et al. | |
| 4,155,012 | 5/1979 | Clarke et al. | 250/563 |
| 4,159,558 | 7/1979 | Durville et al. | 26/10 R |
| 4,271,568 | 6/1981 | Durville et al. | 26/9 |
| 4,297,587 | 10/1981 | Baker | 250/563 |

FOREIGN PATENT DOCUMENTS

| | | | |
|---|---|---|---|
| 369511 | 2/1923 | Fed. Rep. of Germany. | |
| 1295884 | 5/1969 | Fed. Rep. of Germany. | |
| 880174 | 10/1961 | United Kingdom | 66/166 |

*Primary Examiner*—Robert R. Mackey
*Attorney, Agent, or Firm*—Ostrolenk, Faber, Gerb & Soffen

[57] ABSTRACT

The apparatus detects corduroy cutter needles coming out of the weft yarn loop channels which are being cut open by the needles, by means of a laser beam scanning about 10 to 20 times a second, transversely across the region where the parallel needles are working. The scanning laser beam creates a diffused light pattern having the general form of a transversely oriented geometric prism, e.g. a cylinder; and a plurality of detector devices determines any variation in the light distribution, as to time and lateral distance, in this scattered or diffused light pattern. A logic circuit carries out and displays the results of the scanning and detecting, and stops the corduroy cutting machine when an emerged needle is detected.

8 Claims, 3 Drawing Sheets

METHOD FOR DETECTING ANOMALIES IN CORDUROY PREPARATION

This is a division of application Ser. No. 683,592, filed Dec. 19, 1984, now U.S. Pat. No. 4,701,985 granted Oct. 27, 1987.

BACKGROUND OF THE INVENTION

Corduroy velvet textile articles are well known and widely spread in the field of apparel and garments. Corduroy is made, as will be familiar to the man skilled in the art, by preparing a base fabric having lengthwise rows (or ribs) of weft yarn loops protruding upward from the general plane of the base fabric and thus forming lengthwise channels on the fabric. In a separate step, these channels are opened by leading the fabric over a generally flat and horizontal bar, and introducing needle-like cutters into said loop channels, one cutter needle in each channel. When advancing the textile web against these needles and relative shaft—which are arranged in side-by-side relationship over the horizontal bar—the loops are cut and the corduroy velvet is formed. The advancing speed of the web is about from 10 to 20 m/min, typically about 12 m/min.

It occurs rather frequently that a cutting needle pierces the fabric, i.e. it makes a downside exit, or goes upward or sideways out of the respective loop channel, i.e. it makes an upside exit. This occurs since the needles can only be guided at their rear, non-cutting end, and the fabric to be treated is not perfectly homogeneous. In this case, where a needle leaves the channel where it is working, be it downside or upside the channel, the fabric advance must be stopped, and the needle out of order must be located, and properly reinserted into the channel.

Although reinsertion of the needle is a very rapid operation, it is very troublesome to find the needle that is out of order, and it is nearly impossible to detect a defective state of one or more needles when the machine is running and the web is normally advancing.

Electromechanical devices have been proposed to detect outcoming cutting needles. It is easy to detect even one downside outcoming needle, since such a needle is pushed against the metallic bar over which the fabric web is guided for cutting by the very movement of the web, and thereby establishes a fairly good electrical contact. However, upside outcoming needles could hitherto only be detected by electrical contact with a metallic bar placed over the fabric, but this technique is not reliable enough. Detection by the human eye is impractical, rapidly wearing down the physical condition of the supervisor. It must be realized that the number of parallel needles arranged in a needle bed is normally between 600 and 1000. Furthermore, even if the inspecting person, by chance, rapidly detects a needle coming out upside of a loop channel, some time elapses until the machine can be stopped.

It need not be emphasized that a needle coming outside a loop channel will result in faults in the textile material. These faults, namely uncut rows in the produced corduroy, are immediately visible and depreciate the product.

One could imagine the installation of a measuring system over the needle bed and the support bar where loop cutting is performed, based upon changes in capacitance or inductance. However, tests and experiments which have been made show that these systems would not give signals which are sufficiently distinct and characteristic for detecting an emerging needle.

Therefore, there is a need for an apparatus which can rapidly detect needles coming out of a loop row on the upper side of a corduroy fabric web during a cutting operation, regardless of whether the needles emerge at the top or at side locations of the row.

SUMMARY OF THE INVENTION

Thus, it is a first and major object of the invention to provide an apparatus or system to detect needles emerging from weft yarn loop channels at the upper surface of a raw corduroy fabric web wherein the loop channels are to be cut in order to produce corduroy velvet.

Furthermore, another object of the invention is to provide a method for detecting such outcoming needles and to stop the cutting machine immediately in order to reinsert the emerged cutting needle into its loop channel.

Still a further object of this invention is to provide a new and useful corduroy cutting machine equipped with the new needle detecting system.

Another object of the invention is to provide an apparatus of the above-described kind which not only detects emerging needles from the weft yarn loop channels but also detects other faults and deficiencies in the web being fed to the needle bed which would interfere with further treatment of the corduroy, the cutting of the loops included; however, this system should be designed as to discriminate between harmless dust and true faults in the web.

Finally, the system provided by this invention should not only be able to detect emerging cutter needles and other faults but also to give information as to where these faults have occurred.

These objects and still others are met by the invention which, first, provides an apparatus for detecting anomalies in cutting the weft yarn loop rows in the manufacture of corduroy velvet. The apparatus comprises an inspection system for detecting such anomalies without requiring contact with either the material or the needles, comprising a laser-beam scanning unit arranged for projecting a laser beam sweeping substantially at a right angle over the total width of the corduroy web at the location where anomalies are to be detected, and an anomaly detecting device incorporating an integrated logic arrangement and at least one trigger unit for stopping the corduroy cutting machine.

The apparatus further comprises a laser, which is preferably a helium neon laser emitting continuously. The emitted beam is directed to a rotating mirror which creates the horizontal sweep of the beam transversely over the web, at the zone where the outcoming cutting needles are expected. The beam may be divided before sweeping into a number, for example two, of partial beams, each working on a fraction of the width of the web, in order to avoid a too great intensity change during beam sweeping.

Each beam, when travelling over the web, creates up-and-down changes in light power. This change in intensity is detected by a quick photo detecting head. Should a needle have come out of the fabric, the impinging energy at this location is not scattered as on the corduroy but instead is reflected away from the detector. The detector detects at that time a power defect. The defect is amplified, is compared with the background noise, and is processed to give a stop signal when about 16 successive detections have shown the same light power defect. The detector unit comprises a plurality of such detector heads. Each of the partial beams advantageously may scan the web at a rate of about 400 sweeps a second.

The invention further relates to a process for detecting such anomalies; this process comprises projecting at least one transversely sweeping laser beam over the entire width of said web, said beam creating a light band on the zone of the advancing web which is to be inspected for anomalies, said light band producing a light scattering pattern above said zone; monitoring said pattern for intensity changes caused by light reflections from needles emerging from said web or by abnormal light absorption by fabric defects; and translating any anomaly detected during monitoring into a machine stop.

Finally, a corduroy cutting machine is provided comprising the anomaly detecting apparatus as a component.

The invention will now be described further in detail with the aid of the following description of the principles of anomaly detection and of an illustrative example. It is to be understood that the invention is not limited by the following detailed description, but rather that modifications and variations thereon may occur to one skilled in the art within the scope of the invention, as defined by the appended claims.

DETAILED DESCRIPTION OF AN EMBODIMENT OF THE INVENTION

The invention is based on the general principle of the light scattering properties of the textile web surface. In contrast thereto, a needle which has emerged from a loop channel has a distinct reflection pattern, and a fault in the textile web has normally distinctive light absorption properties.

Figure 1:
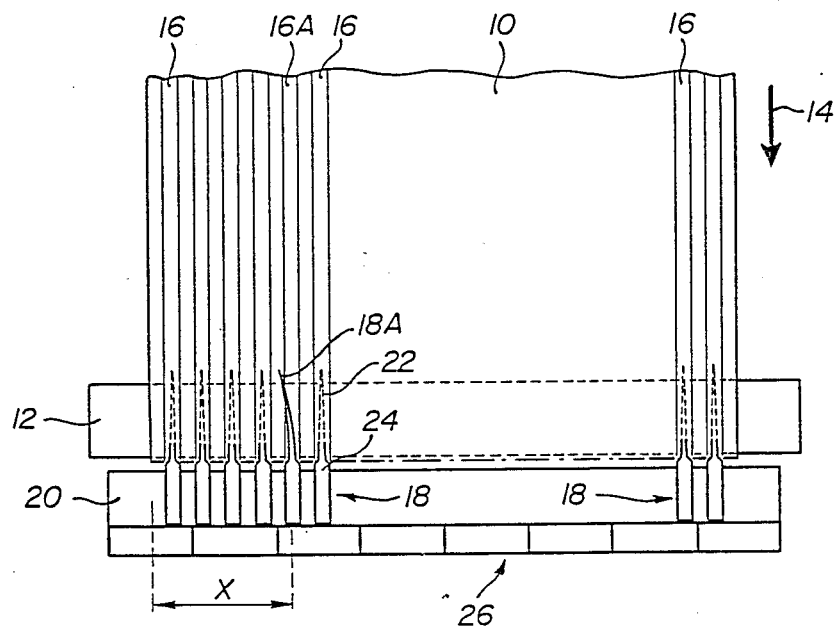
FIG. 1 is a schematic view of a corduroy preparation arrangement showing a cutter needle which has come out of the loop channel.

FIG. 1 is a top view of a corduroy web during cutting. The corduroy web 10 comes from a guide roller (not shown) and travels substantially horizontally in the direction of arrow 14 to a transverse cutting support bar 12. When the corduroy web has gone over the support bar 12, it is deflected downward for further processing.

The corduroy web surface has a plurality of weft yarn loop rows 16 in lengthwise arrangement which form a plurality of protruding ribs. In FIG. 1, only a limited number of rows or channels 16 have been represented for the sake of clarity, and furthermore, the channels 16 are not in scale with the other items of this figure. In reality, there are typically 14 channels per inch of web width, so that a web that is 100 cm (1 meter) wide has about 560 channels or rows of loops.

A plurality of needles 18 (one for each channel) are arranged on a needle bed 20. Each needle cooperates with a particular channel for cutting its loops when the web is travelling in the described manner. Each needle 18 has a cutting shaft 22, inserted in a channel and therefore represented in dashed lines, and a base 24 which also serves as a handle for inserting the needles into the channels. A sectioned needle drive 26 is provided for reciprocating the needles in array form horizontally within the channels 16 in order to facilitate the cutting operation.

All needles shown in FIG. 1 are in good cutting position except needle 18A, which has laterally emerged from channel 16A and is therefore unable to cut the yarn loops of this channel. The machine must be stopped immediately in this situation; otherwise a fault would be created in the corduroy.

Figure 2:
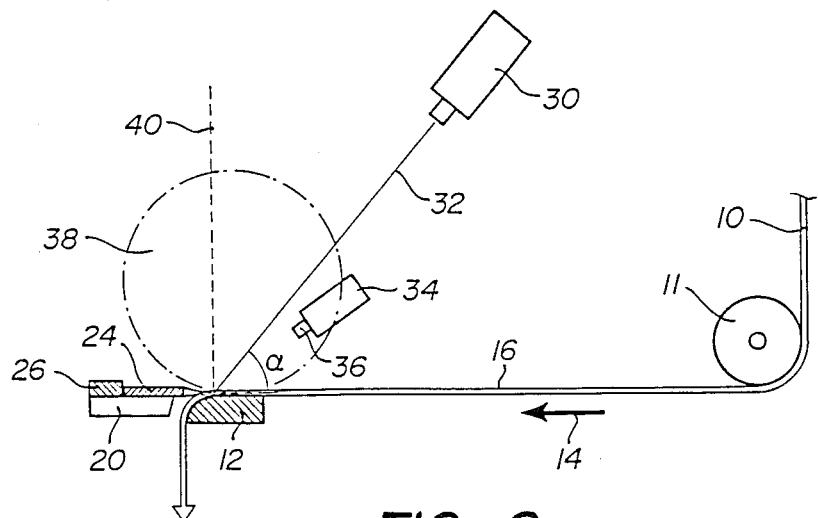
FIG. 2 shows schematically the general arrangement of the laser scanning unit and the detecting devices, relative to the corduroy web, in an embodiment of the invention.

In order to detect such defect, the location of the needles, over the entire width of the web, is scanned by laser light. FIG. 2 schematically shows the general arrangement of the laser unit and the detector unit, in a side view. In FIG. 2, the different items and elements are not necessarily in scale, for the sake of clarity.

As shown in FIG. 1, the corduroy web 10, where the loop channels 16 are not yet cut, travels around a guide roller 11 in the direction of arrow 14 to the support bar 12; a needle is shown (only the needle base 24 is referenced) lying on the needle bed 20 and driven by the needle drive 26.

A laser scanning device 30 is arranged overhead and directs a scanning beam 32 to that part of the machine where the needles 18 are working within the channels. The laser beam 32 sweeps over the entire width of the web 10, as will be described in more detail later, and a narrow light band can be seen when the web 10 is observed from above. A plurality of horizontally aligned detector units 34—of which only one is shown—is directed with its viewing eye 36 toward the light band produced by the reciprocating laser beam on the corduroy surface. These detector units will also be described later.

Since the corduroy surface being processed is raw, undyed optionally bleached corduroy material, a rather large diffusion zone 38 of irregularly scattered light is established adjacent the surface of the web 10 where the laser beam produces the light band. This diffusion zone 38 has a generally cylindrical form; of course, the limits as shown in FIG. 2 are not sharp and are fundamentally arbitrary since the power density decreases from the impact location of the laser beam on the fabric surface into the surrounding space according to the well known reciprocal square law.

The zone 38 shown in FIG. 2 has not necessarily the represented shape. However, all other possible shapes will be substantially symmetrical with respect to the plane 40 which is at a right angle to the web 10 at the location of the laser light band on the web.

Figure 3:
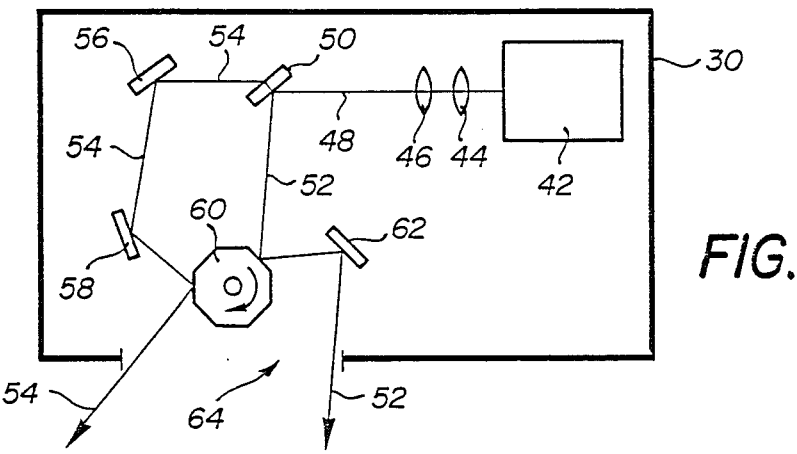
FIG. 3 is a schematic diagram of the laser beam paths to the fabric.

FIG. 3 is a schematic diagram showing the production of the scanning beam. It is to be noted that one of the essentials of the invention is the provision of an energy beam continuously scanning the width of the corduroy web where cutting needles might emerge; in principle, should focusing and energy distribution problems be absent, and further assuming that suitable detectors are available, any energy beam whatsoever could be used, like visible non-coherent light, ultraviolet light, infrared light, as well as invisible energies such as decimeter and centimeter waves, RF waves, etc. For the time being, the laser appears to be the most convenient approach.

In FIG. 3, the housing 30 (see FIG. 2) is schematically represented, and is seen to include a laser 42. Lasers are well known in the art and need therefore not be described in detail here. The laser which is preferably used is a continuously emitting randomly polarized helium neon laser 42. After a focusing stage (collimator lenses 44, 46), the laser main beam 48 is split, by means of a partially reflecting plane-parallel mirror 50, known per se, into a first partial beam 52 and a second partial beam 54, each one of the two partial beams 52 and 54 representing about 50% of the power of the main beam 48. The second partial beam is deflected by a plane mirror 56 such that the deflected beam 54 will travel in about the same direction as the first partial beam 52, but not necessarily parallel to it. Then, another mirror 58 deflects the second partial beam 54 against a rotating mirror 60, which is shown in FIG. 3 as octagonal. The first partial beam 52 is also reflected by the rotating mirror 60, and after having been reflected thereon, the first partial beam 52 is again deflected on a further plane mirror 62 in order to have its transverse movement in the opposite direction with respect to the transverse movement of the second partial beam 54. The two beams leave the housing 30 by the slot 64 which may be covered by a glass (not shown).

Polygonal mirrors may be obtained from low cost glass polygon prisms used in high speed rotary prism cameras. Angle tolerances within 30 arcsec and surface flatnesses within $\frac{1}{4}$ wave are generally sufficient for the purpose of this invention. Such prisms are then aluminum-protected vacuum coated. Finally, the prisms are secured to a circular metal base where, by means of a special design tool, they are easily centered within one hundredth of a millimeter.

These features, along with the provision for trimming means (not shown) either in the mirror mountings or in the polygonal mirror 60, easily allow beam alignment. Bow and wobble combined effects will not exceed +0.5 mm across the maximum corduroy web width.

The system alignment procedure consists essentially in the alignment of this unit with respect to the corduroy cutting machine so as to reach the conditions previously outlined. The housing 30 is then rigidly aligned with the machine when placed on it; the laser beam band is aligned with the tips of the needles 18.

Velvet cutting involves generation of a great amount of dust which is effectively exhausted so as to avoid environmental pollution, or at least to limit it to reasonable levels. In order to make the operation of the laser scanning unit feasible in such a situation, a nearly hermetic pressurized housing 30 has been designed. A pressure is created inside the housing by means of a dust filtered cooling fan, and the laser beams are output through a 10 by 275 mm slot in this example.

This unit 30 may be located about 1.6 m above the cloth, and the laser scanning plane forms with the cloth plane an angle alpha of about 60 degrees (see FIG. 2). Each of the two beams 52, 54 scans the web 10 at a rate of about 400 sweeps per second at a speed of about 1.1 km per sec at the center of the web. These parameter values arise from the boundary conditions of the problem and could be changed easily when applying this system to quite a different machine.

On the web there is only one laser spot at a time. The two laser spots from beams 52 and 54 move symmetrically and alternately in opposite directions, each beginning on the web at about one quarter of the distance from one edge and ending after the other edge has been crossed, and then being replaced by a new beam coming from the next facet of the polygonal mirror 60.

The detector unit 34 is composed of an array of detector heads, aligned in side-by-side relationship on a motherboard (not shown) where they may be plugged in; since the alignment axis is perpendicular to the paper plane in FIG. 2, only the nearest head is shown.

The number and mutual distance of the detector heads depend upon the desired resolution for locating an emerged needle or a fault in the corduroy. For example, five to seven heads will largely be sufficient for 1 meter of web width.

The detector device 34 has an operating distance of about 5 to 10 cm above the web 10 in order to correctly detect any change in the intensity distribution within the diffusion or scattering lobe 38. In order to safely avoid any light influence created by true reflection on emerged cutting needles 18A (FIG. 1), the detector optical axis should be substantially parallel to the laser beam plane 32 (FIG. 2).

As a detector eye 36, a 50 to 10 square millimeter PIN photodiode represents, at the present time, the best choice in view of cost, response speed, sensitivity, ease of use and safety considerations as to operation in an industrial environment. The sensitive area and the construction technology are mainly determinative for spectral sensitivity, overall sensitivity, band width and noise level. A low cost medium performance 7.5 square millimeter component of the type used in color TV remote controls can be used with good results.

Now referring to FIGS. 4A–4E, the detecting situation at all the detecting heads and at a randomly selected one will be considered and explained. In this figure, the D axis represents the distance of a signal detection location from one edge of the web; A represents the signal amplitude in arbitrary units.

Figure 4:
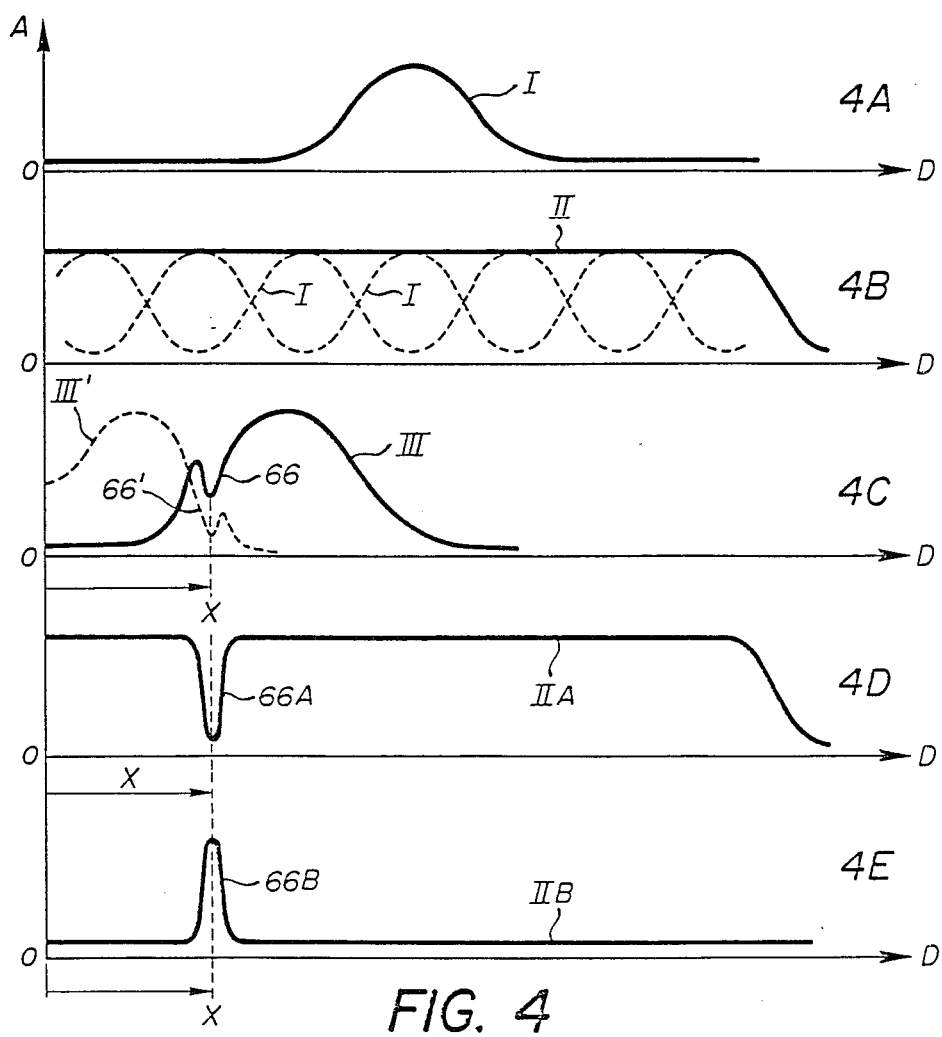
FIGS. 4A-4E represent wave forms for use in explaining the operation of the embodiment.

One of the closely successive partial beams, sweeping over the corduroy web, produces a laterally travelling intensity spot detected by any one of the detector heads, having the form of a bell shaped signal, see curve I in FIG. 4A.

If the lateral distribution and the spacing of all detecting heads of the device 34 (FIG. 2) is properly selected, e.g. for a distance of 6 cm from the web surface, and a spacing of 8.5 cm between adjacent eyes 36, all curves I on successive heads add up to a flat window-shaped signal, see curve II in FIG. 4B, corresponding to a laser spot travel on the web 10 slightly in excess of the total detector array length.

This curve II means that the overall sensitivity of the detector array, expressed by the signal add-up, is no longer dependent on the position of the laser spot. The significance of the basic window signal (curve II) will be further explained later.

When the corduroy web is homogeneous and does not present faults or emerged needles, each detector head detect a bell-like curve, created by the travelling laser beam, shown as curve I in FIG. 4A. The overall sum of the signals of all detector heads, over the width D of the web, is the undisturbed window curve II in FIG. 4B. When needle 18A (FIG. 1) in the lateral position X, measured from the left edge O of the corduroy web, has come out of the channel where it cuts, this zone of the corduroy does not contribute to the formation of the diffused scattered lobe 38 (FIG. 2) since the laser light at that zone is reflected in a rather sharply defined direction and does not impinge on a detector. The same effect is obtained when there is a fault in the web; in this case, the light at the respective location is absorbed rather than scattered. In either case, there is a lack of signal, i.e. a defect signal 66, in bell-shaped curve III detected by, for example, the second detector head. Another defect signal 66', of course at the same distance X, is detected in this example by the first detector, which senses the curve III', see FIG. 4C.

FIG. 4D, the overall window signal IIA is shown which presents the defect signal 66A at the distance X. This signal 66A is the sum of signals 66 and 66', and therefore goes down nearly to zero amplitude.

In order to provide a signal for further processing, an inverting device, for example a NOR gate or a high pass filter, is provided in each detector head. Thus, the inverted overall signal has the form of curve IIB in FIG. 4E, where the defect signal 66A from curve IIA has now become a peak 66B, still at the distance X. FIG. 4E will be discussed further below.

In the circuitry to be described later, this signal 66B is further processed and finally produces at least two distinct outputs: a stop output to stop the machine, and another output to energize suitable indicator devices which indicate in what region over the distance D, i.e. the width of the web, a failure in the web has been produced; normally, there will be as many indicator devices as there are detector heads.

Figure 5:
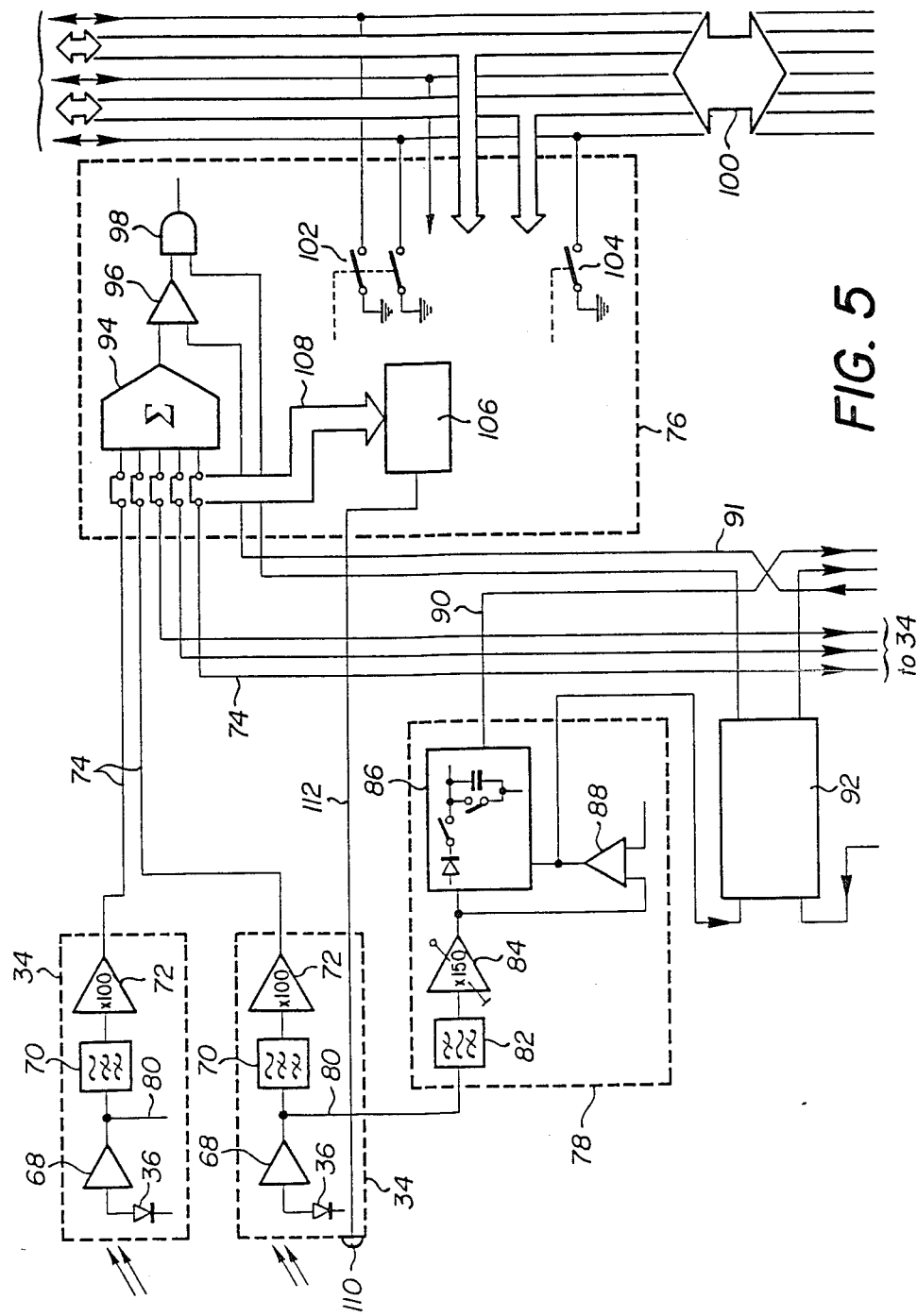
FIG. 5 is a schematic diagram of the overall detecting circuitry.

FIG. 5 shows, in schematic and partial representation, the general electronic circuitry of the detector unit.

FIG. 5 shows only a portion of the detector circuitry; namely, FIG. 5 shows signal processing circuits for five detectors that make up a left half of the detector unit, as seen from the working board of the corduroy cutting machine. Furthermore, only two of the total number of detector heads 34, all identical, are represented. These two detector heads 34, along with three heads that are not shown, generate output signals for further processing on five identical lines 74.

The electronic circuits comprise first the electronics of the detector heads 34 (FIG. 2); two heads are shown which are identical, as are the other detector heads not shown. Each detector head 34 comprises the PIN photodiode 36 already described, a preamplifier 68, a high pass filter 70 and a hundred-fold amplifier 72. The preamplifier 68 amplifies the signals provided by the PIN diode 36 to a level of about 10 mV. This amplified signal is then passed to the filter 70 which is a high pass filter cutting all frequencies below about 80 kHz, since the defect signals 66 and 66' (FIG. 4C) have energy contributions above 100 kHz. The output signal of high pass filter 70 has the form shown in FIG. 4E and is amplified in amplifier 72 to a level of about 1 volt.

On the motherboard, a sum of the five head output signals on lines 74 is performed by a summer 94, that is, a sum of high level pure needle signals instead of bell-shaped signals with superimposed needle contributions. This avoids amplifier saturations due to ambient light. On the other hand, this summing leads to more but still acceptable needle signal contribution overshoot because of the phase spread characteristics of nominally identical filters.

These amplified signals from the left side on lines 74, and in the same way those coming from all heads of the right half of the machine, are transmitted to a respective summer 94 comprising part of a trigger unit 76 which will be described later.

The preamplified PIN diode signals in the heads 34 are not only transmitted to the filters 70, but also, via lines 80, to a brightness detector unit 78 which is now to be described.

Despite the laser scanning unit pressurization, optical components become dusty with prolonged use. Photodiodes also become dusty with use, although they are easily accessible for cleaning. Laser performance degrades with tube age. Polygonal mirror reflectance varies from facet to facet, spreading within a certain range because of random influences or inaccuracies during the coating process. Even the cloth itself can for several reasons slightly change its color. Hence, to compensate for all these events a flat reference signal should be provided, which is tied to light cloud brightness.

On line 80, there appears the bell-shaped signal with embedded needle induced holes, see FIG. 4C. This latter output 80 is used by the motherboard circuitry only from the two heads at positions near the middle of the web, e.g., the two heads 34 shown in FIG. 5, for sampling a spot brightness level just before the laser spot itself crosses the middle of the machine, each such sampling starting the detection process carried out by a respective group of detector heads.

First, the signal on line 80 is processed by a brightness detector 78. The bell-shaped signal III is bandpass-filtered between 4 and 7 kHz in filter 82 in order to reject ambient light influences, needle reflection contributions and electrical disturbances. Then the signal is properly amplified by about 150 times in amplifier 84. In particular, such amplification is adjustable in discrete steps in order to reach the correct system sensitivity during installation. The amplified signal is transmitted to sample-and-hold circuit 86.

The bandpass filtering transforms the bell-shaped signal into something similar to a one-period sinusoidal signal. Amplitudes are still proportional to the laser spot brightness. The sampling process is started by comparison of this signal with a fixed threshold provided by comparator circuit 88. This comparison on the one hand, and circuit saturations on the other, limit the previously outlined compensation to within a certain range. The two sampled brightness signals are then made available as flat reference signals via lines such as lines 90 and 91, for example, to respective comparators 96 in a plurality of trigger circuits 76, each of which treats a group of head needle signals from detectors on the side to which the brightness signal refers, until a new sweep takes place.

The sampling process generates sync signals in a sweep direction detecting logic circuit 92 fed from circuit 88, which allows determination of which side of the detection unit shall next be activated, according to the direction of the sweep that has just started; all trigger circuits are normally disabled except for a proper time window starting immediately after the related brightness sampling process.

Often the corduroy web presents flaws such as cotton impurities, weaving knots, and in general weaving defects which the system must ignore in order to maintain productivity, unless such defects are very big. The channelled structure of the fabric also generates a signal contribution of its own which is quite similar to the needle signal, but fortunately much smaller in amplitude.

Considering in addition the great amplification the signal receives through the circuit (needle holes are about 20 nA at the photodiodes and 8 V at the trigger comparators), a discrimination between background noise and proper fabric defects and needle emerging signals must be made, to avoid false machine stops with consequent productivity degradation (external disturbances may be due to radio-frequency interference (RFI) and line voltage disturbances, for example; internal disturbances may be due to commutating logic, i.e. RFI and power line disturbances and transients caused by bistable logic components switching between states).

The needed reliability mentioned above is accomplished by means of a rough numerical filtering. That is, in order to stop the machine, it is necessary that the same group of heads detects a needle out of the fabric (i.e. that signal holes exceed the predetermined reference level) during a number of consecutive laser sweeps. This number is typically in the order of 5 to 20, preferably 16. Every time a sweep fails, one more sweep is needed (the sweep count cannot be negative). As soon as the predetermined count is reached, a stop signal is issued on a global bus 100 (by the closure of the switches 102, in this example), which causes the machine to stop and lock in such a state (a stop-and-lock signal being issued).

These functions are performed in the trigger circuit 76 where all head signals, coming from lines 74, are added in a summing circuit 94. The output of circuit 94 is transmitted, as well as the related brightness signal (flat reference signal) from circuit 78, to a comparator 96 and then to a needle-detected gate 98.

Trigger circuit 76 further contains the stop-and-lock switch unit 102, a count preset device, and a timeout preset brake switch 104.

The stop signal can be cancelled, allowing operation to resume, only upon a reset pulse issued by a power supply/power interface unit (not shown) as a consequence of an operator intervention.

Sixteen sweeps may represent too long a response time for a given type of machine where fabric speed is in the range of 200 mm per second. Therefore, after a minimum count, presettable in the power supply/power interface unit, is reached, a preliminary signal is issued on another line (brake signal on global bus 100) which causes fabric feed to stop.

After such a signal has gone active there is a presettable timeout in the power supply/power interface unit, in terms of the number of sweeps to reach a count of sixteen and consequently lock the machine in the stop state, requiring operator intervention. Otherwise, the brake signal is removed and operation is automatically resumed; in practice the machine instantaneously slows fabric feed.

A practical realization of the invention has been constructed, which consists in a 59 cm long motherboard with seven detection heads 34, two brightness/sync circuits 78 and three triggers 76. Brightness circuits 78 are connected to the second and to the sixth heads 34.

Each trigger 76 can be operated with up to five consecutive detection heads 34, which can be located also on the next motherboard, depending on the mounting of the input jumpers associated with the summer 94, as seen in FIG. 5, or the mounting of sum resistors, if any. Hence, adjacent head groups can be overlapped as needed.

Connections between motherboards have been arranged in a straightforward way (flat cable 1-to-1 connections) separately for signals (global bus, brightness and sync side signals plus consecutive detection head outputs) and supplies.

A power supply/power interface unit hooks at either one of the two sides of the chain of motherboards indifferently just as if it were a further motherboard (except that connection involves only global bus signals and power supply rails).

Such an architecture allows modularity in a conceptually non-modular system without having to introduce redundancies. All detecting heads are identical.

All motherboards also are identical, except that some sections can be mounted or not, and some sum resistors can be inserted to connect detection head outputs or not (brightness and sync circuits, for example, are mounted only in the mid-board).

Trigger circuit 76 furthermore comprises a distance discriminator 106 to which signals coming from heads 34 are transmitted via bus 108. Circuit 106 detects from which region of the laser beam band on the corduroy surface a stop signal has come and energizes, via line 112, a respective display 110 (only one of them is shown). This may be an LED; of course, its light is to be shielded from photodiode 36. A cancelling circuit (not shown) cancels signals from circuit 106 when the machine is started again.

There is further a power supply/power interface unit which is not represented in a figure. The functions of this unit are indicated clearly by its name and from the previous discussion. The unit performs the functions described above and furnishes the necessary power and voltage. Since the particular layout and construction is easily conceived by the man skilled in the art, the power supply/power interface unit need not be described in detail.

Although embodiments of the invention have been described herein, the invention is not limited to such embodiments. Rather, various modifications may occur to one skilled in the art within the scope of the invention, as defined in the claims.

We claim:

1. A method of detecting web anomalies in a cutting machine for the manufacture of corduroy fabric webs, such as a cutting machine which is operable for advancing a corduroy base web having lengthwise rows of weft yarn loops over a horizontal supporting bar to a plurality of needle-like cutters for introduction of a cutter into each yarn loop to effect severing of the weft rows, the method comprising:

projecting at least one laser beam to sweep over a path that is substantially transverse to the advancing direction of said web, over the total width of the web and at the location where the needle-like cutters are working within the weft yarn loops and the web is being fed to said cutters, detecting an intensity of light from the laser beam diffused by the web or caused by light reflectance from emergence of one of said needle-like cutters from a respective weft row, of caused by abnormal light absorption by web defects, detecting changes in said intensity indicative of such anomalies in the web, namely such emergence of cutters or such defects, generating an anomaly signal in response to such detected changes, for indicating detection of an anomaly in the web; and generating a signal for stopping the corduroy cutting machine and the advance of the web in response to an anomaly signal.

2. A method according to claim 1, wherein the laser beam is provided by employing a laser to continuously emit a main beam, dividing the main beam into two partial beams each representing about 50% of the main beam, and employing a rotating mirror device to produce two sweeping beams capable of covering the two halves of said web, said two sweeping beams overlapping each other in the middle section of the web and overshooting the edges of the web.

3. A method according to claim 1, including employing a level-responsive logic circuit for processing said anomaly signal and thereby preventing false stop signals due to noise caused by background illumination or dust.

4. A method according to claim 4, including effecting a machine stop when a true anomaly has been detected but avoiding false stops, by considering a predetermined number of laser beam sweeps, each causing an anomaly signal, to define a true anomaly.

5. A method according to claim 4, includng providing an indication of at which portion of the width of the web an anomaly has been detected, when said stopping signal is generated.

6. A method of detecting web anomalies in a cutting machine for the manufacture of corduroy fabric webs, said cutting machine having cutter needles for cutting weft yarn loops of a corduroy fabric web which is fed to said cutter needles, comprising the steps of:

creating a light band by projecting light toward the portion of the web where the cutter needles are working within the weft yarn loops and the web is being fed to said cutters, thereby producing a light scattering pattern above the zone;

monitoring said pattern for intensity changes caused by anomalies such as fabric web defects and the emergence of cutter needles from weft yarn loops of the corduroy fabric web; and stopping said cutting of said corduroy fabric web in response to the detection of any anomaly;

wherein said light band is created by sweeping at least one laser beam transversely over the width of said web; and wherein the laser beam is provided by employing a laser to continuously emit a main beam, dividing the main beam into two partial beams, and employing a rotating mirror device to produce two sweeping beams capable of covering the two halves of said web, said two sweeping beams overlapping each other in the middle section of the web and overshooting the edges of the web.

7. A method as in claim 6, wherein the light scattering pattern is monitored by detectors which detect the increase and decrease of light intensity produced by the sweeping laser beam, and detect anomalies due to reflection or absorption of light by identifying a defect signal in the curve of increasing and decreasing light intensity.

8. A method as in claim 6, wherein the location of the web where an anomaly has been detected is indicated at the time the cutting process is stopped.

* * * * *